United States Patent [19]

Doulakas

[11] Patent Number: 4,829,088

[45] Date of Patent: May 9, 1989

[54] MEDICAMENT FOR THE TREATMENT OF INFLAMMATIONS OF THE EYE

[75] Inventor: Johann Doulakas, Winterthur, Switzerland

[73] Assignee: Dispersa AG, Hettlingen, Switzerland

[21] Appl. No.: 38,316

[22] Filed: Apr. 14, 1987

[30] Foreign Application Priority Data

Apr. 14, 1986 [DE] Fed. Rep. of Germany ....... 3612537

[51] Int. Cl.$^4$ .......................................... A61K 31/195
[52] U.S. Cl. ..................................... 514/567; 514/914
[58] Field of Search ............... 514/496, 658, 669, 914, 514/970, 567

[56] References Cited

U.S. PATENT DOCUMENTS 4,518,608  5/1985  Kahan ................................. 514/420

FOREIGN PATENT DOCUMENTS 3026402   2/1982   Fed. Rep. of Germany .
58-174310 10/1983  Japan .
58-174309 10/1983  Japan .
2059768   4/1981   United Kingdom .

OTHER PUBLICATIONS

Dolder et al., Opthalmika, Stuttgart 1983, pp. 401–415.
The Merck Index, Tenth Edition (1983), No. 9575.
Chemical Abstracts, 100, No. 2, Jan., 1984; No. 12683W.

Primary Examiner—Douglas W. Robinson
Attorney, Agent, or Firm—Wenderoth, Lind & Ponack

[57] ABSTRACT

The invention relates to an ophthalmic medicament containing diclofenac-sodium in aqueous solution. Owing to the addition of a specific stabilizer, the medicament has excellent stability against chemical decomposition of the active ingredient and outstanding preservation properties and is tolerated very well by the eye.

6 Claims, No Drawings

MEDICAMENT FOR THE TREATMENT OF INFLAMMATIONS OF THE EYE

The invention relates to a medicament for the local treatment of inflammations of the eye that contains diclofenac-sodium as the active ingredient, has a more stable formulation and is tolerated very well by the eye.

Hitherto, predominantly corticosteroids have been used for the treatment of relatively severe acute or chronically recurrent inflammatory symptoms in the eye. The immunosuppressant action of these substances, however, conceals the risk of a deterioration in the clinical picture as a result of a bacterial or viral infection. Recently, therefore, strenuous efforts have been made to develop non-steroidal anti-inflammatory agents and to introduce them into ophthalmological therapy.

Diclofenac-sodium, having the chemical name sodium 2-(2,6-dichloroanilino)-phenyl acetate, is a known non-steroidal anti-inflammatory agent; cf. DE-C 1 543 639 and DE-C 1 793 592. Its forms of administration include all forms of tablets, capsules and dragees and also suppositories and ampoules.

The active ingredient has hitherto been used mainly in otorhinolaryngology, gynaecology, urology, paediatrics and rheumatology. In addition, however, the substance has also been used systemically in ophthalmology. A disadvantage of this type of use is that only a relatively low level of action is achieved at the site of action via the systemic route, and it cannot be assumed that an increase in the dose will result in a corresponding increase in the local level of action.

The topical administration of diclofenac-sodium to the eye should bring advantages here in two respects: firstly, it will not be necessary to burden the entire organism with the active ingredient in order to obtain a local effect and, secondly, a locally higher level of action will be obtained with an eye drop solution.

A diclofenac-sodium-containing solution for administration to the eye is known from JP-A-58/174310. The eye drops described in that publication contain diclofenac-sodium in a concentration of from 0.01 to 1%. They have a pH of preferably 7 to 8. Phosphates, boric acid, borax and organic acids are used as buffers. Sodium chloride and mannitol are named as isotonising additives. Polyoxyethylene sorbitan monooleate, polyoxyethyleneoxystearic acid triglyceride, polyoxyethylene glycol and $\alpha$- and $\beta$-cyclodextrin are mentioned as solution aids. Polyvinylpyrrolidone, methylcellulose, hydroxypropylmethylcellulose and hydroxypropylcellulose are specified as thickeners. In addition, benzalkonium chloride, cetylpyridinium chloride, chlorobutanol and thiomersal are named as preservatives. Finally, pharmacologically tolerable calcium or magnesium salts are added, customarily in an amount of from 0.3 to 2 mol per mol of active ingredient, in order to reduce eye irritation.

The addition of calcium or magnesium salts of physiologically tolerable acids in order to reduce eye irritation caused by anti-inflammatory eye drops that contain as active ingredient a non-steroidal anti-inflammatory agent having a carboxy group in the molecule is also described in JP-A-No.58/174309.

The eye drop formulations described in JP-A-Nos. 58/174310 and 58/174309 have considerable disadvantages, however, which make them unsuitable for use as finished medicaments.

A considerable disadvantage of the known formulations is that they are unstable in the compositions described.

Also, in the case of eye drops, there is a statutory requirement in most European and other countries that the preparations should be preserved, that is to say protected against attack by micro-organisms and the subsequent multiplication thereof. Although JP-A-No. 58/174310 gives information on the possible use of preservatives, the preservatives specified are unsuitable for the mentioned purpose in the formulations described for the following reasons: benzalkonium chloride and cetylpyridinium chloride are incompatible with diclofenac-sodium without the addition of a suitable solution aid; their addition results in a precipitation in the preparation. Benzalkonium chloride is also incompatible with polyoxysorbates as proposed as solution aids in JP-A-No. 58/174310. Chlorobutanol is stable only at a pH of less then 6 and is therefore not suitable for use in preparations that have a pH of from 7 to 8. Thiomersal, which is also named as a preservative in JP-A-No. 58/174310, is incompatible with the sodium chloride which is contained in the described formulations in order to produce isotonia. Furthermore, thiomersal is itself unstable in aqueous solution. The formulation examples given in JP-A-No. 8/174310 do not mention a preservative.

A further disadvantage of the known formulations is that calcium or magnesium salts have to be added in order to prevent eye irritation by the active ingredient or by $\beta$-cyclodextrin which is the preferred solution aid. The addition of calcium and magnesium salts to the formulations has proved to be undesirable since the alkaline earth ions may form complexes with the active ingredient thereby impairing the latter's availability and stability.

For the reasons given, it is not possible according to the prior art to obtain diclofenac-sodium-containing eye drops that are stable and preserved in conformity with statutory requirements and that do not irritate the eye.

The problem underlying the invention is therefore to formulate diclofenac-sodium in the form of eye drops that have sufficient stability for a finished medicament, are preserved in conformity with requirements and are well tolerated by the eye.

This problem is solved by the surprising finding that, by using specific stabilizers, on the one hand sufficient stabilization of the active ingredient can be achieved and at the same time, on the other hand, it becomes possible to use a preservative since the problems of stability and compatibility associated with its use are solved. Finally, it has also been found that, in the invention described here, it is not necessary to use calcium or magnesium salts to eliminate eye irritation.

The invention therefore relates to a sufficiently stable, preserved, well tolerated and effective medicament for the treatment of inflammations of the eye that contains an aqueous solution of diclofenac-sodium, a buffer, an isotonising agent, a solution aid and a preservative. The medicament is characterised in that it contains an aminopolyol as the stabilizer for the active ingredient and the preservative.

By the addition according to the invention of a specific stabilizer to the aqueous diclofenac-sodium preparation intended for use as eye drops, the difficulties associated with the known diclofenac-sodium-containing eye drops are eliminated.

2-amino-2-hydroxymethyl-1,3-propanediol (trometamol) and its homologues having up to 10 carbon atoms, especially from 5 to 7 carbon atoms, have proved especially suitable for the desired purpose.

Trometamol and its homologues having up to 10, preferably from 5 to 7, carbon atoms can also be illustrated by the general formula I:

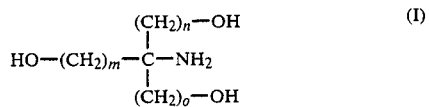

in which m, n, and o (independently of one another) each represents an integer of at least 1 and the sum of m, n and o is in the range of from 3 to 9, preferably from 3 to 6.

Especially preferred is 2-amino-2-hydroxymethyl-1,3-propanediol (trometamol) that corresponds to a compound of the formula I in which $m=n=o=1$.

By adding these stabilizers, the decomposition of the diclofenac-sodium, which would otherwise occur during storage, is prevented in an effective manner. In addition, the use of a preservative is made possible, this preservative being necessary per se to prevent the preparation from being attacked by micro-organisms and being required by law. In particular, thiomersal, which has especially advantageous preservative properties but is unstable per se in aqueous solution, can be used in the formulation of the invention since it is co-stabilized indirectly by the stabilizer used. The stabilizer prevents the thiomersal from being adsorbed at the container wall thereby decisively improving its storability. Finally, it has been found that no eye irritation occurs with the formulation of the invention, so that it is not necessary to add calcium or magnesium salts, which are undesirable because of the active ingredient.

The individual constituents of the ophthalmic medicament of the invention are described below.

The active ingredient, diclofenac-sodium, is used in a concentration of from 0.01 to 0.15%, preferably from 0.05 to 0.11%. An active ingredient concentration of approximately 0.1% is especially preferred.

The pH of the formulation is preferably from 6.8 to 7.5. There may be used as buffer substances, for example, boric acid, borates, phosphates and organic acids. The use of boric acid is preferred, the stabilizer added, for example trometamol, acting as the basic component of the buffer mixture.

The boric acid used as buffer substance is used preferably in such an amount that at the same time isotonia of the formulation is obtained. Optionally, it is also possible to use glucose, citrates, phosphates, borates or other known substances as isotonising agents.

In order to avoid problems of compatibility with the thiomersal, sodium chloride is not used to isotonise the preparation when thiomersal is used as the preservative. On the other hand, however, sodium chloride can be used when benzalkonium chloride or cetylpyridinium chloride is used as the preservative.

As solution aids for the diclofenac-sodium there are used in the preparations of the invention, for example, fatty acid glycerol polyglycol esters, fatty acid polyglycol esters, polyethylene glycols, glycerol ethers or mixtures of those compounds. Specific examples of especially preferred solution aids are reaction products of castor oil and ethylene oxide, for example the commercial product Cremophor EL ®. Reaction products of castor oil and ethylene oxide have proved to be especially good solution aids having excellent eye tolerability. The concentration used depends principally on the concentration of the active ingredient. At least a sufficient amount should be added to dissolve the active ingredient. For example, the concentration of the solution aid is from 1 to 100 times, especially from 5 to 60 times, the concentration of the active ingredient.

A preservative must be present in the preparations of the invention in order to prevent an attack by micro-organisms during the period of administration. Owing to its excellent preservative properties, the sodium salt of 2-(ethylmercurithio)-benzoic acid (thiomersal) is especially preferred for the purpose. It is used in a concentration of from 0.002 to 0.02%, preferably from 0.002 to 0.005% and especially approximately 0.004%. Apart from thiomersal, it is also possible to use other known preservatives, such as benzalkonium chloride or cetylpyridinium chloride, in a concentration of from 0.005 to 0.02%. Combinations of the mentioned substances with the disodium salt of edetic acid are also suitable.

The stabilizer is added to the preparation of the invention in an amount of from 0.05 to 5%, preferably from 0.1 to 1.0%. In that amount the stabilizer, as mentioned, brings about both stabilization of the active ingredient against chemical decomposition and stabilization of the preservative, thiomersal, against decomposition in aqueous solution. Furthermore, the stabilizer additionally ensures that the preservatives benzalkonium chloride and cetylpyridinium chloride which can also be used according to the invention are compatible with the active ingredient. When using these preservatives it may be necessary slightly to increase the amount of solution aid.

The preparation of the invention is formulated with water for injection purposes. An osmolality of approximately 0.9 (301 mosmol/kg) is established.

Owing to its excellent chemical stabiity, the preparation of the invention can be stored for a relatively long period even at room temperature and meets the requirements demanded of such a preparation in respect of its stability during therapeutic use.

The medicament of the invention is manufactured in a manner known per se by mixing all the components of the medicament homogeneously, and filling them, under sterile conditions.

The following formulation examples illustrate the invention:

EXAMPLE 1

| Constituent | Amount |
| --- | --- |
| diclofenac-sodium | 0.1% |
| 2-(ethylmercurithio)-benzoic acid, sodium salt | 0.004% |
| boric acid | 1.9% |
| trometamol | 0.6% |
| Cremophor EL ® | 5.0% |
| water for injection purposes | ad 100% |

EXAMPLE 2

| Constituent | Amount |
| --- | --- |
| diclofenac-sodium | 0.1% |
| benzalkonium chloride | 0.01% |
| boric acid | 1.9% |
| trometamol | 0.6% |
| Cremophor EL ® | 5.0% |

-continued

| Constituent | Amount |
| --- | --- |
| water for injection purposes | ad 100% |

EXAMPLE 3

| Constituent | Amount |
| --- | --- |
| diclofenac-sodium | 0.1% |
| cetylpyridinium chloride | 0.01% |
| boric acid | 1.9% |
| trometamol | 0.6% |
| Cremophor EL ® | 5.0% |
| water for injection purposes | ad 100% |

The formulations of Examples 1, 2 and 3 will keep for from 3 to 5 years at room temperature.

The tolerability of the eye drops was investigated in an eye irritant effect and toxicity study. The eye drop solution investigated corresponds to formulation example 1. The r®st solution is applied to the conjuctival sac five times a day over a period of four weeks. Two groups of six rabbits each are used for the study.

The following test scheme is used:

| group | male | female | right eye | left eye |
| --- | --- | --- | --- | --- |
| 1 | 3 (389–391)* | 3 (395–397)* | untreated | physiological saline |
| 2 | 3 (392–394)* | 3 (398–400)* | eye drops without active ingredient | eye drops with 0.1% diclofenac-Na |

*Number assigned to the animal

The animals are examined for eye irritation twice a day, befre the first and after the final daily administration.

The following is a summary of the results of the investigation:

After the four-week treatment with 50 μ 1 of the 0.1% diclofenac-sodium eye drop solution, none of the rabbits exhibits either symptons of local irritation or systemic symptons.

Schirmer's test is carried out as a specific investigative method for determining increased lacrimation resulting from local irritation:

| Schirmer's test (Measurement time: 2 minutes, measurements in millimeters) | | | | | | |
| --- | --- | --- | --- | --- | --- | --- |
| animal number/ sex | before the test | | after 2 weeks | | after 4 weeks | |
| | left | right | left | right | left | right |
| Group 1 | | | | | | |
| 389/m | 7 | 6 | 9 | 6 | 6 | 5 |
| 390/m | 3 | 5 | 8 | 5 | 5 | 6 |
| 391/m | 4 | 9 | 4 | 5 | 4 | 7 |
| 395/f | 5 | 4 | 4 | 7 | 5 | 6 |
| 396/f | 7 | 11 | 8 | 6 | 6 | 8 |
| 397/f | 5 | 8 | 4 | 7 | 4 | 5 |
| average | 5.2 | 7.2 | 6.2 | 6.0 | 5.0 | 6.2 |
| Group 2 | | | | | | |
| 392/m | 8 | 7 | 3 | 6 | 2 | 8 |
| 393/m | 8 | 10 | 6 | 5 | 10 | 9 |
| 394/m | 5 | 4 | 5 | 7 | 4 | 9 |
| 398/f | 7 | 10 | 5 | 12 | 5 | 6 |
| 399/f | 4 | 8 | 7 | 6 | 5 | 2 |
| 400/f | 5 | 5 | 3 | 6 | 4 | 7 |
| average | 6.2 | 7.3 | 4.8 | 7.0 | 5.0 | 6.8 | m = male
f = female

Observations and measurements obtained with Schirmer's test show there are no differences between treated eyes and control eyes that can be linked with the eye drops tested.

The differences that do occur can be regarded as individual cases having no biological or toxicologial significance.

To summarize, it can therefore be stated that the administration of the diclofenac-sodium-containing eye drop solution referred to in this patent specification as formulation example 1 to the eye of the rabbit over a period of four weeks is safe. This investigation at the same time demonstrates the local tolerability of the adjuncts.

A supplementary 7-day irritant effect study was carried out on rabbits for the additive trometamol. Two groups of six animals each are again used.

| test group | 1 | | 2 | |
| --- | --- | --- | --- | --- |
| dosage | (1) | | (2) | |
| sex | m | f | m | f |
| number of test animals | 3 | 3 | 3 | 3 |
| observations and findings deviating from the norm | none | none | none | none |

(1) Group 1
left eye: NaCl solution 0.9%
right eye: 0.5% trometamol
(2) Group 2
left eye: buffer
right eye: 2% trometamol The eyes are examined twice daily, before the first and after the final administration. To summarise the result, trometamol is well tolerated by the eye of the rabbit.

The good tolerability proved in the animal experiment could be demonstrated also within the framework of clinical tolerability tests on humans. 221 people are treated with eye drops corresponding to formulation example 1. Apart from an occasional brief and slight stinging immediately after administration, no specific side effects are observed.

Overall, therefore, the results lead to the conclusion that the present formulation is a solution for ophthalmological use that is tolerated well locally.

I claim:

1. In a medicament for the treatment of inflammations of the eye, containing an aqueous solution of diclofenac-sodium in an amount of from 0.01 to 0.15%, a buffer, an isotonising agent, a solution aid and a preservative, the improvement wheein the medicament contains a compound of the general formula I

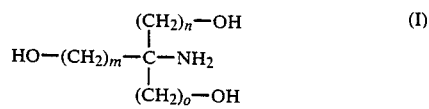

in which m, n, and o, independently of one another, each represents an integer of at least 1 and the sum of m, n and o is in the range of from 3 to 9, in an amount of from 0.05 to 5% as stabilizer for the active ingredient and the preservative and also as additional buffer.

2. A medicament according to claim 1, containing 2-amino-2-hydroxymethyl-1,3-propanediol as stabilizer.

3. A medicament according to claim 2, containing the sodium salt of 2-(ethylmercurithio)benzoic acid as preservative.

4. A medicament according to claim 2, containing benzalkonium choloride as preservative.

5. A medicament according to claim 2, containing cetylpyridinium chloride as preservative.

6. A medicament according to claim 1, containing a 0.05 to 0.11% aqueous solution of diclofenac-sodium, boric acid in an amount of 1.9% as buffer and isotonising agent, a reaction product of castor oil and ethylene oxide in an amount of 5.0% as solution aid, the sodium salt of 2-(ethylmercurithio)benzoic acid in an amount of from 0.002 to 0.005% as preservative and 2-amino-2-hydroxymethyl-1,3-propanediol in an amount of from 0.1 to 1.0% of stabilizer.

* * * * *

UNITED STATES PATENT AND TRADEMARK OFFICE
CERTIFICATE OF CORRECTION

PATENT NO. : 4,829,088

DATED : May 9, 1989

INVENTOR(S) : JOHANN DOULAKAS

It is certified that error appears in the above-identified patent and that said Letters Patent is hereby corrected as shown below:

Column 8, line 11, change "of" to --as--.

Signed and Sealed this

Twenty-fourth Day of April, 1990

Attest:

HARRY F. MANBECK, JR.

Attesting Officer

Commissioner of Patents and Trademarks